(12) United States Patent
Sunseri (10) Patent No.: US 11,226,319 B1
(45) Date of Patent: Jan. 18, 2022

(54) METHOD FOR ASSESSING ABILITY TO DISTINGUISH CONSUMABLES

(71) Applicant: Aimée Sunseri, Sacramento, CA (US)

(72) Inventor: Aimée Sunseri, Sacramento, CA (US)

( * ) Notice: Subject to any disclaimer, the term of this patent is extended or adjusted under 35 U.S.C. 154(b) by 250 days.

(21) Appl. No.: 16/592,722

(22) Filed: Oct. 3, 2019

Related U.S. Application Data (60) Provisional application No. 62/741,116, filed on Oct. 4, 2018.

(51) Int. Cl.
| | | |
|---|---|---|
| *G01N 33/14* | (2006.01) | |
| *G01N 33/02* | (2006.01) | |
| *G01N 37/00* | (2006.01) | |
| *G01N 33/00* | (2006.01) | |

(52) U.S. Cl.
CPC ....... *G01N 33/0001* (2013.01); *G01N 33/146* (2013.01); *G01N 33/02* (2013.01); *G01N 37/005* (2013.01)

(58) Field of Classification Search
CPC .... G01N 33/0001; G01N 33/02; G01N 33/14; G01N 33/146; G01N 37/005
USPC ............................................. 436/20, 24, 161
See application file for complete search history.

(56) References Cited

U.S. PATENT DOCUMENTS

| | | | | |
|---|---|---|---|---|
| 7,124,035 | B1* | 10/2006 | Tomlinson | G06Q 30/02 |
| | | | | 702/23 |
| 7,167,815 | B2 | 1/2007 | Labreche | |
| 8,920,175 | B2* | 12/2014 | Black | G16H 20/60 |
| | | | | 434/127 |
| 9,784,722 | B2 | 10/2017 | Tompkins | |
| 9,810,674 | B2* | 11/2017 | Mikami | A23K 20/10 |
| 9,891,201 | B2 | 2/2018 | Hort | |
| 2009/0026167 | A1* | 1/2009 | Metry | G09F 3/0288 |
| | | | | 215/386 |
| 2011/0287133 | A1* | 11/2011 | Ortega | C12G 1/00 |
| | | | | 426/2 |
| 2016/0376537 | A1* | 12/2016 | Saerens | C12N 1/20 |
| | | | | 426/13 |

OTHER PUBLICATIONS

Mchael O'Mahony, Who told you the triangle test was simple?, Food Quality and Preference 6 (1995) 227-238, Elsevier Science Limited, Amsterdam, Netherlands.

Joachim Kunert & Michael Meyners, On the triangle test with replications, Food Quality and Preference 10 (1999) 477-482, Elsevier Science Limited, Amsterdam, Netherlands.

Michael O'Mahony, Who told you the triangle test was simple?, Food Quality and Preference 6 (1995) 227-238, Elsevier Science Limited, Amsterdam, Netherlands.

\* cited by examiner

*Primary Examiner* — Maureen Wallenhorst
(74) *Attorney, Agent, or Firm* — Bert P. Krages, II (57) ABSTRACT

A method of use encompassing coded sampling containers that may be implemented in two phases, the results of which may be further processed to arrive at a final score. The first phase incorporates four sampling containers in the context of a series of triangle tests to arrive at a first subscore. The second phase uses two of the coded containers and requires the participants to assess the degree to which the contents of the containers reflect a particular characteristic on a scale. The responses of each participant may be scored by summing the differences between the actual answers and the correct answers to arrive as a second subscore. A final score may be calculated by subtracting the first subscore from the second subscore.

19 Claims, 6 Drawing Sheets

METHOD FOR ASSESSING ABILITY TO DISTINGUISH CONSUMABLES

BACKGROUND OF THE INVENTION

Enthusiasts of beverages and foods typically have different levels of proficiency at evaluating the sensory characteristics of the beverages or foods for which they are enthusiastic. For example, there exists an established wine enthusiast culture in which members pride themselves on their ability to discern the various characteristics of wines. In addition to enthusiasts, many people find pleasure in evaluating their ability to discern differences in the taste and aroma of beverages or food irrespective of their degree of familiarity with the subject matter The triangle test is a method used to assess whether a discernable difference is present between two beverage or food products. During a triangle test, a plurality of participants is presented with a set of three samples in which one is different and two are alike. There are six possible combinations in which two products, designated as A and B, may be presented: AAB, ABA, ABB, BAA, BBA, and BAB. The participants are instructed to identify the odd sample and record their answers. The data are evaluated using the chi-square distribution: $X^2=\Sigma(|O-E|)^2/E$, where O equals the observed number of correct answers and E equals the expected number of correct answers. In a triangle test, the probability of a correct answer by chance is $\frac{1}{3}$. The probability of choosing an incorrect answer by chance is $\frac{2}{3}$. Whether or not the participant are able to discern a statistically-significant difference between products A and B can be assessed using a chi-square distribution in which the actual number of correct answers is compared with the expected number of correct answers.

The ability of humans to evaluate taste and odor varies depending on factors such as physical condition, experience with a foodstuff, and even anatomy. It is further understood that humans generally do not distinguish between individual chemical substances individually, but express the taste of various chemical substances as a whole. Furthermore, interactions can occur between taste substances, such as a suppression effect or a synergistic effect. Despite the differences in the ability of individuals to discern specific sensory characteristics of foods and beverages, it is well known that a consensus view of sensory characteristics can be established, for example, that a particular wine can be discerned as having specific "notes."

SUMMARY OF THE INVENTION

The invention encompasses coded sampling containers and may be implemented in two phases, the results of which may be further processed to arrive at a final score. The first phase incorporates a series of triangle tests to arrive at a first subscore. The second phase uses two of the coded containers and requires the participants to assess the degree to which the contents of the containers reflect a particular characteristic on a scale. The responses of each participant may be scored by summing the differences between the actual answers and the correct answers to arrive as a second subscore. A final score may be calculated by subtracting the first subscore from the second subscore.

The first phase of the invention permits the execution of a new variation of the triangle test in which a single participant is given a set of four samples from which various subsets of three samples will be selected during a series of tasting rounds. Two of the samples in the set will consist of Product A and two of the samples will consist of Product B. It is important that Product A and Product B differ with respect to at least one characteristic that affects the flavor, aroma, or feel of the beverage or food. Ideally, the recipes for the manufacture of Product A and Product B will differ with respect to one parameter or one ingredient. For example, a wine could be manufactured using the same varietal of grapes grown on the same lot and with identical processing with the exception of aging Product A in a barrel made from American oak and aging Product B in a barrel made from French oak. Similarly, a beer could be manufactured using the same malt, adjuncts, water, and processing times, but in which Product A is made using one variety of aroma hops and Product B is made using a different variety.

To prepare the test, amounts of Product A are placed into two containers that are each coded with two different code symbols in accordance with a predetermined pattern. Similarly, amounts of Product B are placed in two other containers that are coded with two different code symbols in accordance with the pattern. The code symbols may consist of any distinct form that identifies the samples such as a geometric shape, a letter, or a number. Examples of coded containers are stem tags on wine glasses, adhesive labels on containers, and beverage glasses, cups, plates, bowls, and baskets onto which the code symbols have been written, etched, or otherwise marked.

The predetermined pattern may also be selected from a set of predetermined patterns. For example, a set could consist of the following patterns:

Pattern 1: Product A (■▲) Product B (●★)
Pattern 2: Product A (■●) Product B (∈▲)
Pattern 3: Product A (▲●) Product B (★■)

In addition to the code symbol that has been assigned to each container, each container may likewise bear a plurality of code symbols that differentiate the samples from each other. An illustrative example would be a set of four wineglasses in which two glasses contain Product A and two glasses contain Product B in accordance with Pattern 1, and which bear additional symbols, form the following matrix:

| Product $A_1$ | Product $A_2$ | Product $B_1$ | Product $B_2$ |
|---|---|---|---|
| ■ | ▲ | ● | ★ |
| D | N | G | F |
| H | K | I | S |
| A | G | O | Y |
| U | P | R | M |

The participant then tastes the samples in a series of rounds in which three samples are selected from the set of four samples in accordance with a table of predetermined combinations. After tasting the three samples in each round, the participant records which sample is believed to be different from the other two samples. The predetermined combinations ensure that the series of trials encompass different subsets of the samples. For example, the predetermined combinations could involve the following samples in which the combinations reflect words that are formed by the letters contained in the matrix, as is illustrated below:

| Round Number | Product Combination | Geometric Symbols | Word |
|---|---|---|---|
| 1 | $B_2\,A_1\,A_2$ | ★■▲ | FUN |
| 2 | $B_1\,A_1\,A_2$ | ●■▲ | OAK |
| 3 | $A_1\,B_1\,B_2$ | ■●★ | DRY |
| 4 | $B_2\,B_1\,A_2$ | ★●▲ | SIP |

-continued

| Round Number | Product Combination | Geometric Symbols | Word |
|---|---|---|---|
| 5 | $B_1 A_2 B_2$ | ●▲★ | GEM |
| 6 | $A_1 B_1 A_2$ | ■●▲ | AGE |

The participant then completes the remaining rounds and records the symbol which represents the sample that is believed to be different from the other two. Whether the participant has answered correctly is determined by comparing the answer to a key that is specific to the pattern. The answer key may encompass the words used in to express the predetermined combinations, with the letter assigned to the container having the sample that is different from the other two samples being denominated typographically, such as boldface, italics, or underscore. An example of such an answer key is shown below, which is specific to the previously described Pattern 1.

| Round Number | Word (correct answers in boldface and underscore) |
|---|---|
| 1 | FUN |
| 2 | SIP |
| 3 | DRY |
| 4 | OAK |
| 5 | GEM |
| 6 | AGE |

Once the participant has made the determination of which answers were correct, the number of correct answers is totaled to arrive at the first subscore. The answers may also be evaluated in accordance with a statistical test, such as the chi-square test, to determine whether the participant's correct answers are significantly better than what would be expected by chance.

As stated previously, the second phase uses two of the coded containers to hold different samples and requires the participants to assess the degree to which the contents of the containers reflect a plurality of characteristics on a scale. Depending on the desired embodiment, the participants can evaluate the characteristics of the contents of each container independent of the other container or they can evaluate the characteristics of the contents of one container relative to the contents of the other container.

For example, sophisticated wine enthusiasts who are highly familiar with the sensory characteristics of wines might find it more challenging to evaluate the characteristics of the two wines independently. In such as case, after tasting the first sample, the participants evaluate the presence of the first characteristic and rate it on a scale of choices, such as 0 to 4, where a 0 indicates that the characteristic is absent, a 4 indicates that the characteristic is very strongly present, and 1, 2, and 3 indicate respectively that the characteristic is mildly present, moderately present, and strongly present. After the participants make their ratings, the ratings are recorded on a score sheet. The participants then do the same for the remaining characteristics for that sample, following which the participants repeat the same steps for the second sample.

In another example, participants who are less familiar with the ranges in which the various sensory characteristics are generally expressed in wines, may find it more satisfying and educational to do a comparative evaluation. In such a case, one of the sample containers is deemed to contain the wine that is used as the reference and, after tasting the wines in both containers, the participants record the degree of the difference between the wines in the two containers and record their assessments in terms of the degree of difference. In such as case, the participants might record the relative presence of the sensory characteristics in the second wine in terms of much less, less, the same, more, or much more.

Each participant is scored according to how close their ratings are to the correct rating to determine a second subscore for each participant. The second subscore consists of the sum of the differences between the participant's answer and the correct answer for each characteristic of the two samples. In the example described above for independent evaluations, the absolute values of the difference between a participant's ratings and the correct answers would be summed. For the example given for the comparative evaluation, the number of spaces of a participant's rating from the correct answer would be summed. A final score for each participant can be calculated by subtracting the first subscore from the second subscore.

DETAILED DESCRIPTION OF THE PREFERRED EMBODIMENT

A specific preferred embodiment of the invention is described in the following text. The description makes reference to various elements that are further depicted in the drawings. This description and the drawings employing reference in which a specific number is used to label each element in a drawing and same number is used to label that element in the associated drawings and to refer to that element in the following description. The drawings should be used collectively with respect to the discussion of the elements in the description.

The preferred embodiment involves a kit encompassing two bottles of wine of identical manufacture save one component, coded wine glasses, instructions, and score sheets. A plurality of participants uses the kit to conduct a two-part evaluation of the wine in the bottles. The objective encompassed by the first part of this embodiment is to assess the ability of participants to discern whether they can detect the difference between a wine that has been bulk aged in barrels made from American oak from a wine that has been bulk aged in barrels made from French oak. It is known in the winemaking industry that the type of oak used in the barrels will affect the complexity of the flavor depending the type of wine that is being oaked. In this regard, it is possible for a winemaker to prepare two wines from a single harvest of grapes and with common processing, fermentation, and clarification, but which are bulk aged in barrels made from oak trees grown in either France or the United States.

Figure 1:
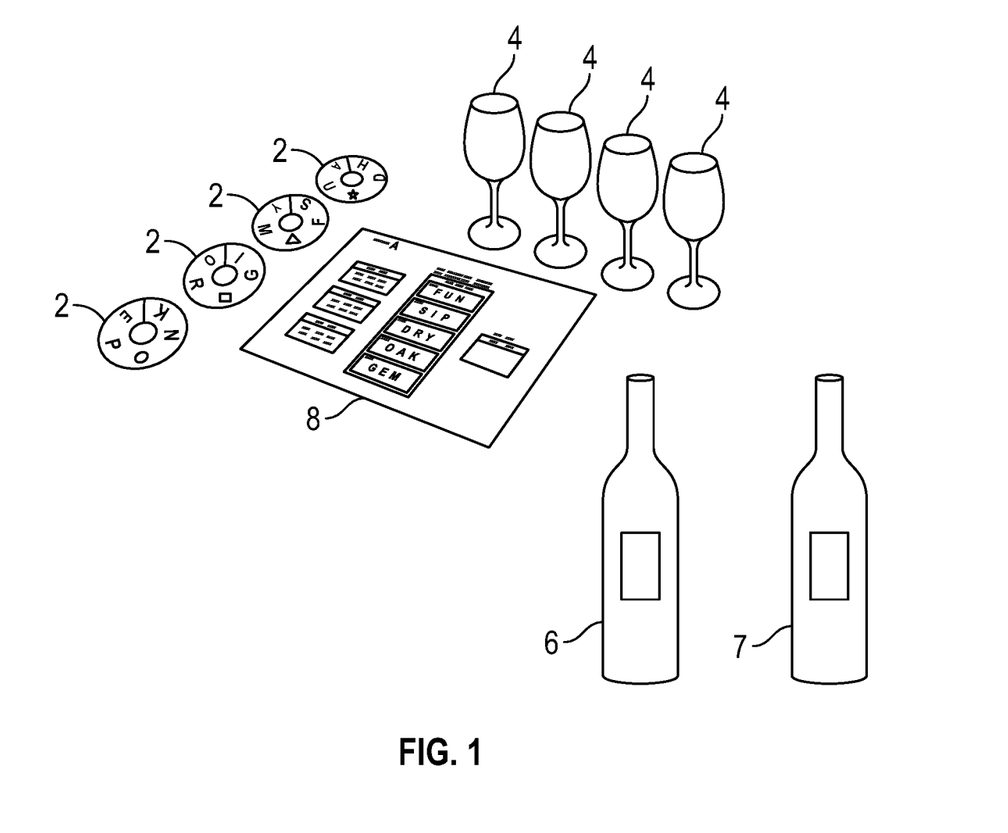
FIG. 1 is a drawing showing components used to carry out the method.

To carry out the first phase of the preferred embodiment, each of the participants is given four stem tags 2 as shown in FIG. 1. Each stem tag contains four different letters and a geometric symbol. Each stem tag 2 is used to identify one of four glasses 4 given to each participant. The kit is supplied with a first and second bottle of wine made from Semillon grapes. The wine in both bottles is made from the same batch of grapes with identical processing except the wine in the first bottle 6 is aged in barrels made from oak grown in the United States and the wine in the second bottle 7 is aged in barrels made from oak grown in France. The participants will use the score sheet 8 to record their selection of a pattern and their scores in accordance with the method described below.

Figure 2:
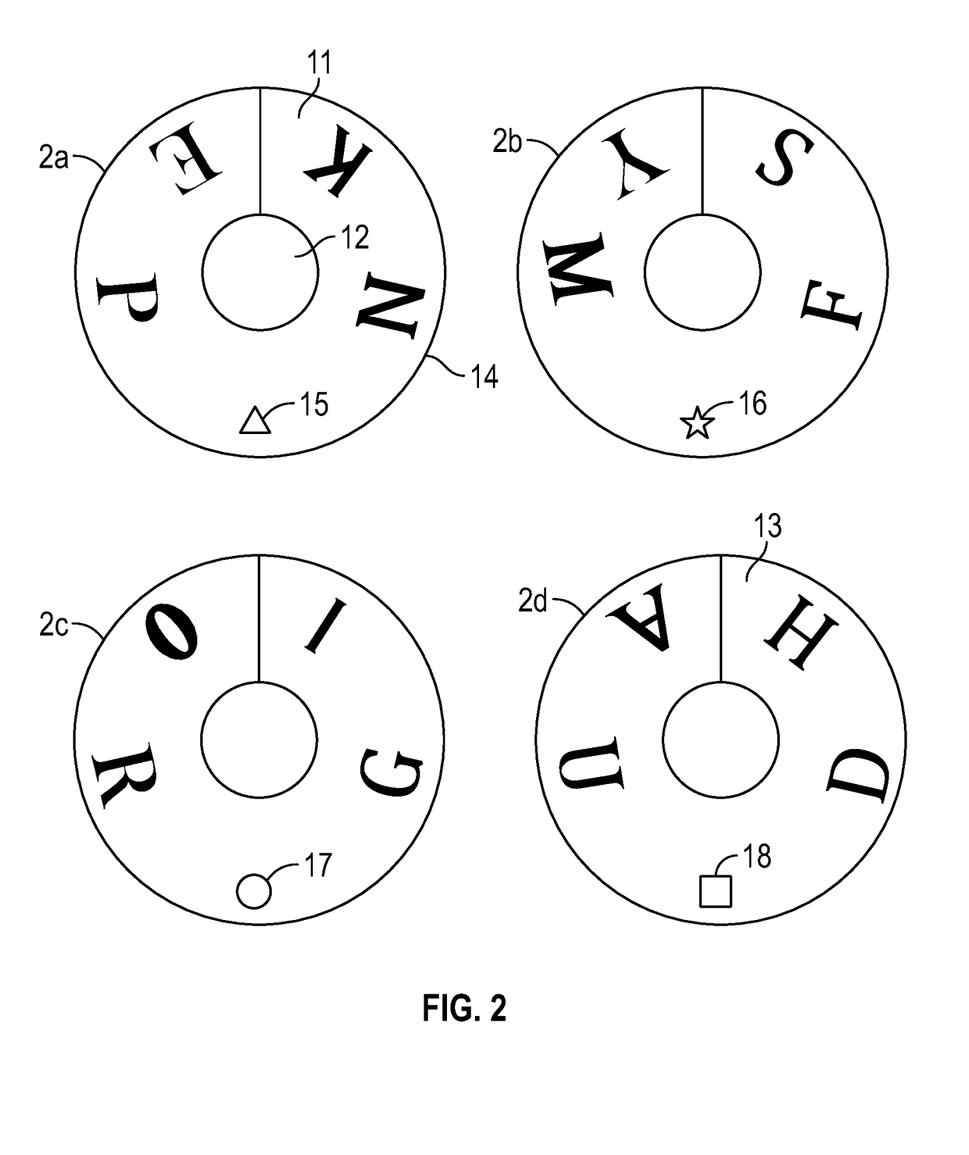
FIG. 2 is a drawing showing the stem tags used to code the wine glasses.

The stem tags, as shown on FIG. 2 have a top side 11 and a bottom side (not shown) which is blank. A circular shape is preferred and each stem tag has an empty circular space 12 in the center and a cut 13 running from the circular space 13 to the edge 14 of the stem tag. The top side 11 for each stem tag has letters and a geometric symbol that are different for each stem tag. In the preferred embodiment, the first stem tag 2a has the letters E, K, P, N and a triangle 15, the second stem tag 2b has the letters F, M, S, Y and a five-pointed star 16, the third stem tag 2c has the letters G, I, O, R and a circle 17, and the fourth stem tag 2d has the letters A, D, H, U and a square 18.

Figure 3:
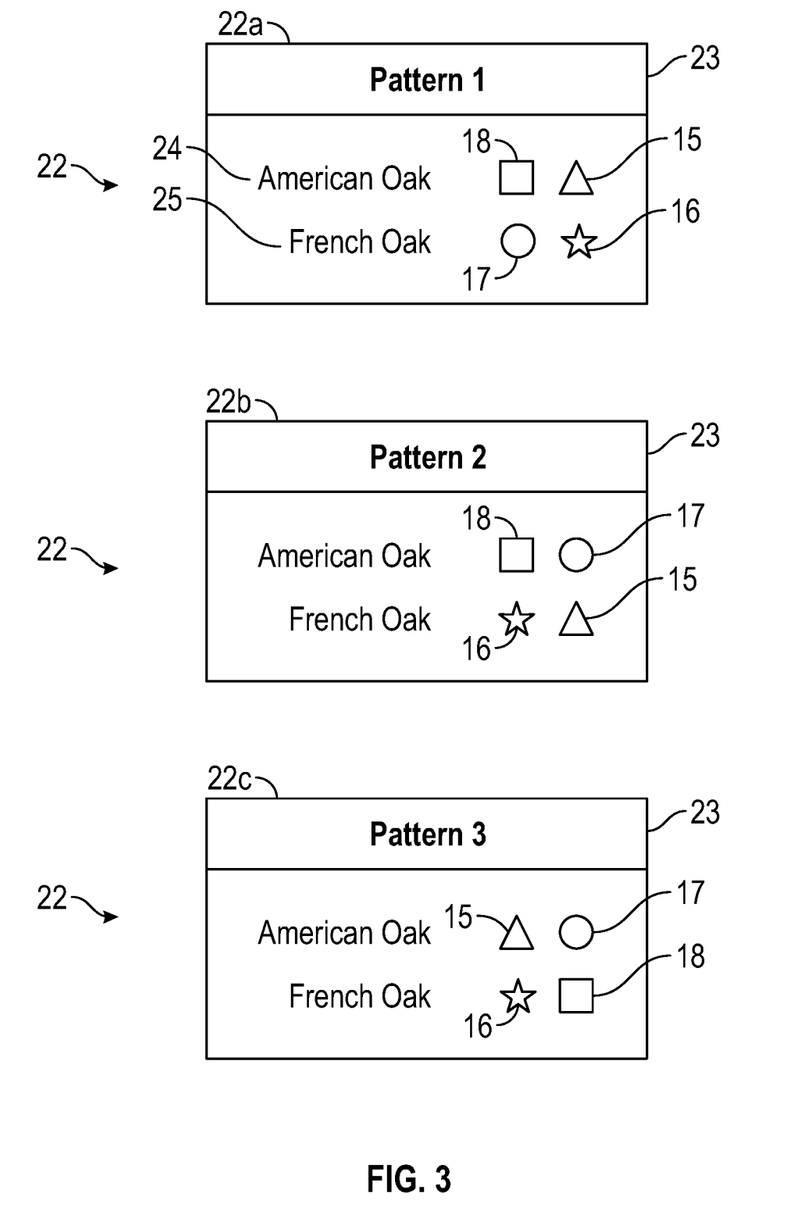
FIG. 3 is a drawing showing a predetermined selection of patterns by which to assign samples of a first and second wine to specific wine glasses.

As shown in FIG. 3, a plurality of patterns 22 is provided to the participants. Each pattern has an identifying pattern number 23, an American oak identifier 24 associated with two geometric symbols and a French oak identifier 25 associated with two different geometric symbols. The preferred embodiment encompasses three patterns 22 of which the first pattern 22a associates wine aged in American oak barrels with a triangle 15 and a square 18 and wine aged in French oak barrels with a circle 17 and a star 16. Similarly, the second pattern 22b associates wine aged in American oak barrels with a circle 17 and a square 18 and wine aged in French oak barrels with a triangle 15 and a star 16 and the third pattern 22c associates wine aged in American oak barrels with a triangle 15 and a circle 17 and wine aged in French oak barrels with a star 16 and a square 18. Each participant selects a pattern 22 and writes the pattern number 23 on the bottom side of the four stem tags 2 shown in FIG. 1 that have been assigned to that participant. The purpose of writing the pattern number 23 on the bottom of the stem tags 2 is to maintain a record of the pattern number 23 while at the same time concealing that information from the other participants.

Figure 4:
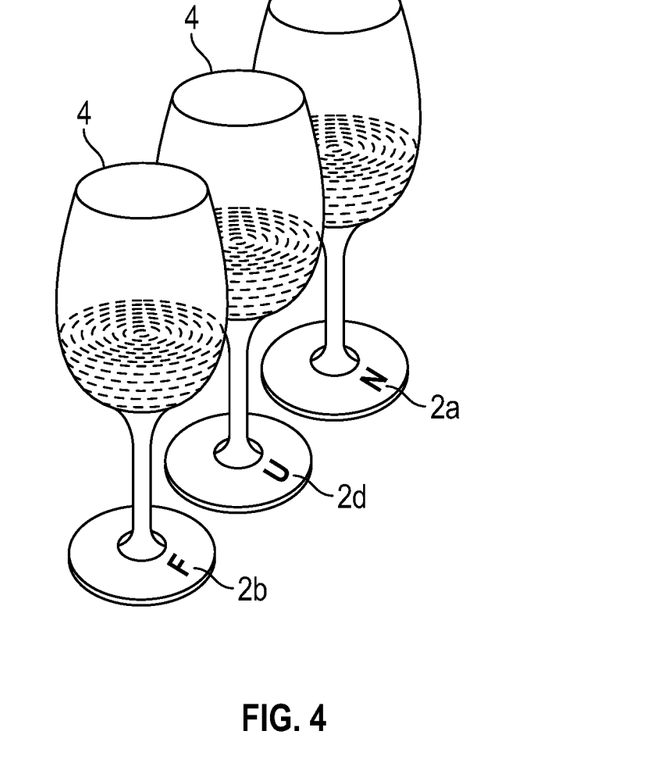
FIG. 4 is a drawing showing wine glasses bearing coded stem tags such as to spell a three-letter word.

Each participant attaches a stem tag 2 to each of the four wine glasses 4 and pours into each glass either wine from the first bottle 6 (American oak) or the second bottle 7 (French oak) in accordance with the pattern 22 that the participant has selected. The participants then exchange their sets of wine glasses 4 so that each participant has a set made by another participant and is unaware of the pattern number of the set in his or her possession. Each participant then selects three of the wine glasses 4 such that the letters on the stem tags form a preselected three-letter word. For example, if the preselected three-letter word is FUN, the participants would select the wines in glasses bearing the stem tags 22a, 22b, and 22d as shown in FIG. 4.

Figure 5:
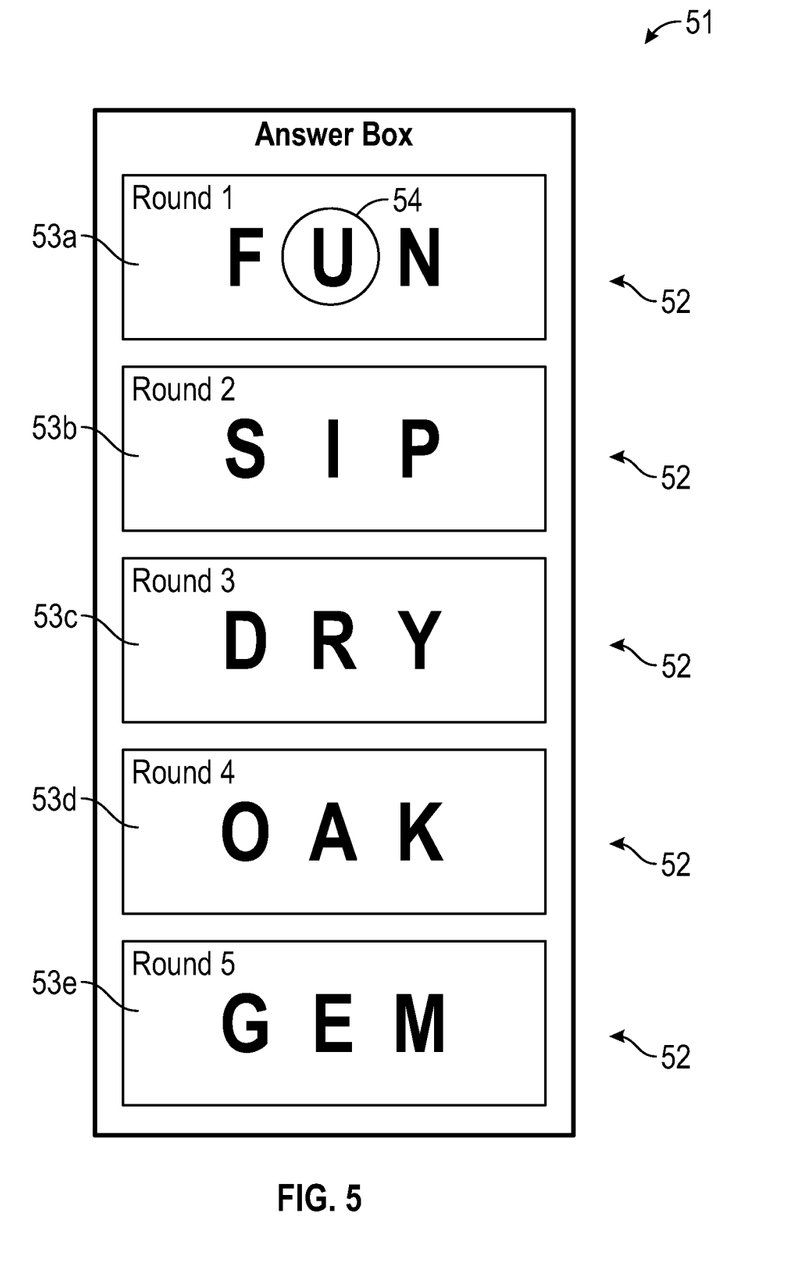
FIG. 5 is a drawing showing an answer box used by a participant to record determinations made during the first phase of the method.

Each participant conducts a first round of sampling in which they taste the wine from each of the three wine glasses 4 bearing the stem tags 22a, 22b, and 22d and makes a determination of which glass contains the wine that is different from the wine in the other two glasses. This determination is recorded in an answer box 51 as shown in FIG. 5. In the preferred embodiment, the answer box 51 contains five partitions 52 with each partition containing a round designation 53a-e as well as letters that correlate to a letter on one of the stem tags 2 and in which three of the letters for a three-letter word. For example, if a participant during the first round samples wines from the glasses 4 bearing stem tags 22a, 22b, and 22d (as shown in FIG. 4) and determines that the wine in glass bearing stem tag 2d is different from the wine in the glasses bearing stem tags 22a and 22b, then the participant would apply a marking 54 around the letter U in partition 53a.

The process of selecting three wine glasses 4 from the sets of four glasses then continues through second, third, fourth, and fifth rounds with the selections determined by the letters in the preselected three-letter words. In the preferred embodiment, the second round is associated with the word SIP, the third round is associated with the word DRY, the fourth round is associated with the word OAK, and the fifth round is associated with the word GEM. The words for each round are selected to ensure that each round of sampling encompasses a different combination of the two wines. During each round, the participants make their determinations of which glass 4 contains wine that is different from the wine in the other two glasses and records their determinations on the answer box 51.

After the fifth round is completed, each participant flips over a stem tag 2 to determine the pattern by which the wines have been poured into the wine glasses 4. An answer key is then consulted and the number of correct determinations by each participant is summed to determine their scores for the first phase of the embodiment. It should be noted that getting five correct determinations indicates that the participant is ranked at a level having 99 percent statistical significance and getting four correct determinations indicates that the participant is ranked at a level having 95 percent statistical significance. In the preferred embodiment, each participant is assigned a point for each of their correct answers in the first part and the number of points are summed to provide a score for the first phase. For example, if a participant made four correct determinations, the score for that participant would be "four."

The second phase of the embodiment assesses the ability of the participants to distinguish differences in the characteristics of the two wines. Preferably, the degrees of the presence of the characteristics are based on analyses of the wines using gas chromatography. In the preferred embodiment, the specific characteristics and the associated analytical parameters are as follows:

charred/smokey guaiacol
vanilla vanillin
clove eugenol and isoeugenol
baking spice 4-methylguaiacol
freshly cut oak cis oak lactones
coconut trans oak lactones
sweet/almond 5-methylfurfural To commence the second phase, the glasses 4 are emptied and rinsed. Each participant pours about two ounces of wine from either the first bottle 6 (American oak) and a second glass is filled with about two ounces of wine from the second bottle 7 (French oak) into the glass bearing the stem tag 2b which contains a geometric symbol in the shape of a star 16, as shown in FIG. 2. If a participant poured wine from the first bottle 6 into the glass bearing stem tag 2b, then that participant will next pour about two ounces of wine from the second bottle 7 into the glass bearing stem tag 2c, which contains a geometric symbol in the shape of a circle 17. However, if a participant poured wine from the second bottle 7 into the glass bearing stem tag 2b, then that participant will next pour about two ounces of wine from the first bottle 6 into the glass bearing stem tag 2c, which contains a geometric symbol in the shape of a circle 17. In this way, the wine glasses 4 bearing stem tags 2b and 2c will contain wines from the different bottles 6 and 7. In either case, the participants write on the bottom side of the wine stems which wine has been poured into each glass. It is further desirable that the participants not disclose to their fellow participants which wine has been poured into which glass.

Figure 6:
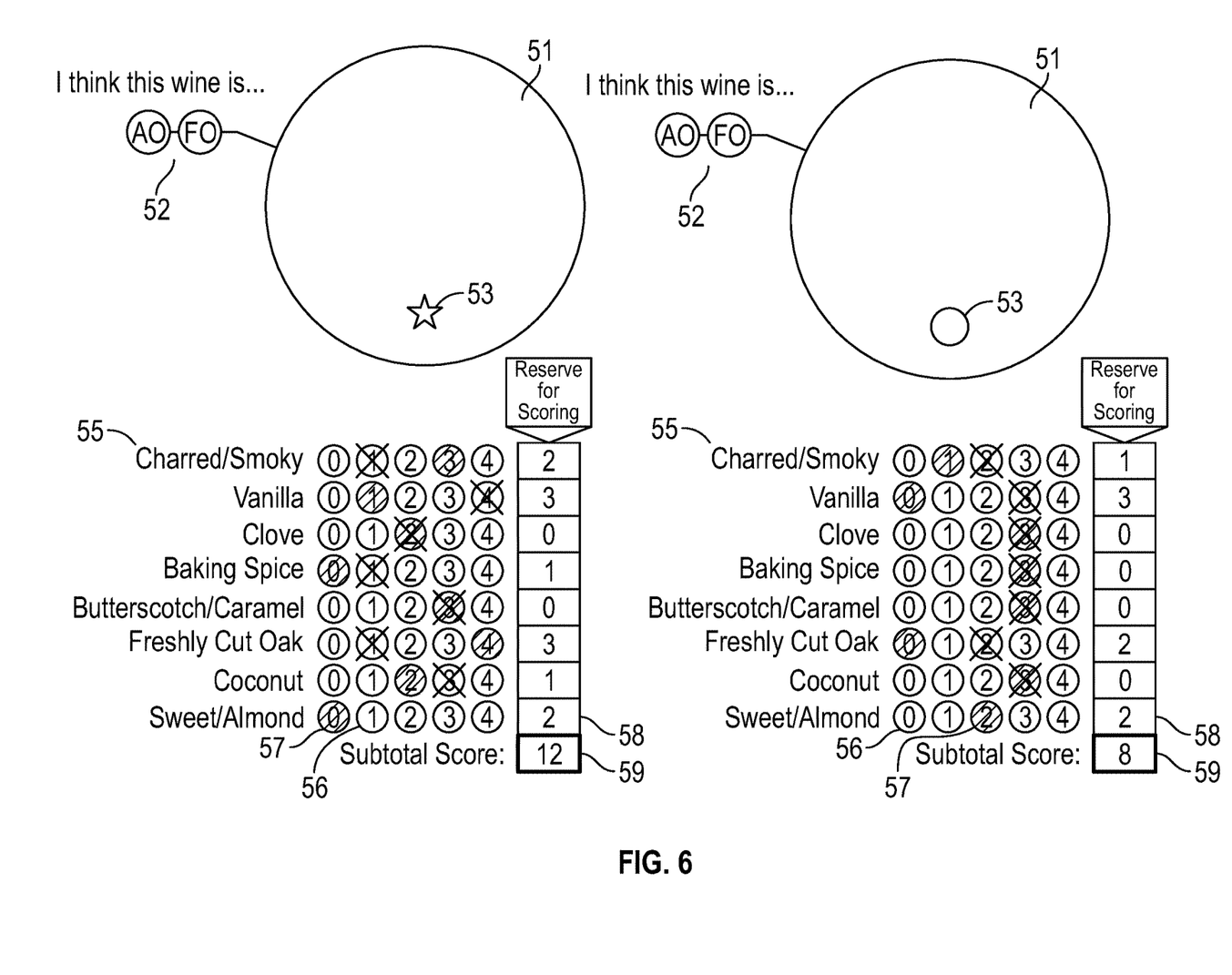
FIG. 6 is a drawing showing an answer sheet used by a participant to record determinations made during the second phase of the method.

FIG. 6 depicts the arrangement used for scoring for the preferred embodiment in which the wines in bottles 6 and 7 are independently evaluated with respect to the selected characteristics. In this variant, two circles 51 are marked on a surface, with each circle 51 having a diameter approximately equal to the diameter of the foot of the wine glasses 4. The circles are respectively designated by a geometric symbol 53 in the shape of a star or a circle. Each participant is assigned a surface and places the glass 4 bearing stem tag 2b is placed on the circle 51 having the geometric symbol 53 in the shape of a star and places the glass 4 bearing stem tag 2c on the circle 51 having the geometric symbol 53 in the shape of a circle. The participants then exchange places so that the participants will not know from which bottle 6 or 7 has been poured into which glass 4 on the surface in front of them.

Each participant samples the wines by smelling the aroma, tasting the wine, or both and evaluates the wine in each glass 4 according to specific aromas, which are indicated on the surface by a label 55 which is associated with five bubbles 56 numbered consecutively from zero to four. In one variation of the preferred embodiment, the participants use their personal discretion in the manner in which they evaluate the wines. For example, a participant can choose to evaluate all the specified aromas associated with the wine in one of the glasses before proceeding to the wine in the other glass or, alternatively, a participant may choose to evaluate one of the aromas of both glasses before proceeding to evaluate another aroma. Conversely, in other variations of the embodiment the participants may be required to conduct the evaluations in a predetermined order of steps.

Either during the course of sampling the wines or shortly thereafter, the participants mark the bubble 56 with the number that in their mind best reflects the intensity of the characteristic associated with the label. In this regard, a bubble 56 with the number "zero" would reflect a determination by a participant that none of the characteristic was present in the wine whereas the number "four" would reflect a determination that characteristic was very intense. For example, a participant who determined that the wine in the glass 4 marked with a star did not possess any "sweet/almond" aroma would fill in the bubble with the "zero" 57. Similarly, if the same participant were to determine that the wine in the glass 4 marked with a circle had a moderate amount of the "sweet/almond" characteristic, he or she would fill in the bubble with a "two" 57.

Once all the participants have finished recording their determinations, those determinations are scored by consulting an answer key and marking the bubbles 56 that correctly reflect the degree to which the wines possess the characteristics by drawing an "X" through those bubbles 56. The difference between the participants' determinations and the correct answers are assigned a number ranging from 0 to 4 based on the absolute value of the difference between the numbers in the bubble 56 marked a participant's determination and the bubble 56 marked with the correct answer. The resulting values are then recorded in a column 58 for each characteristic. For example, if a participant marked a bubble 56 with a "three" as the determination for the presence of "charred/smokey" and the correct answer was reflected by the bubble 56 with a "one," the value of "two" would be placed in the entry space associated with "charred/smokey" in the column 58. Similarly, if the participant marked a bubble 56 with a "one" as the determination for the presence of "vanilla" and the correct answer was reflected by the bubble 56 with a "four," the value of "three" would be placed in the entry space associated with "vanilla" in the column 58.

Once all the determinations by a participant are scored, the figures are summed for each column 58 and the sum is placed in the box 59 for the subtotal score. The subtotal scores in the two boxes 59 are then summed to determine the total score for the second phase. In the context of determining which of the participants was the most adroit at evaluating the wines, the score from the first phase is subtracted from the total score from the second phase to obtain a final score. The participant having the lowest final score is thus deemed the most adroit. In the event that two or more participants have the same final score, they can further mark their assessments of which wine was in the respective glasses 4 in an assessment space 52. The participant or participants who correctly identify the wines are thus deemed more adroit than the participants who make an incorrect identification.

The variant of the embodiment in which the wines are evaluated comparatively is largely similar. However, in such a case if the reference wine is that contained in the glass 4 bearing stem tag 2b, then the provisions for scoring may be limited to the glass 4 bearing stem tag 2c. Thus, the participants sample the wines by smelling the aromas, tasting the wine, or both and evaluates how much the wine in the glass 4 bearing stem tag 2c differs from that of the wine in the glass 4 bearing stem tag 2c. The participants' ratings of the differences are then recorded in bubbles 56. Although a scale of zero to four may be used in which "zero" indicates that the characteristic is absent, a "four" indicates that the characteristic is very strongly present, and "one," "two," and "three" indicate respectively that the characteristic is mildly present, moderately present, and strongly present, it is easier for the participant if the bubbles 56 are aligned in columns labeled "much less, "less," "the same," "more," and "much more." Alternatively, the participants could do a comparative evaluation based on which of the wines in each glass 4 have a stronger presence of a sensory characteristic. In such a variant, the sensory characteristics are indicated on the surface by a label 55 which is associated with five boxes 56 ranging between the two samples, such as much more, more, same, more and much more. Thus, the sample in the glass bearing stem tag 2b is associated with the much more or more on the left side of the answer sheet, and the sample in the glass bearing stem tag 2c is associated with the more or much more on the right side of the answer sheet. The same option is in the middle of the five choices. Either during the course of sampling the wines or shortly thereafter, the participants mark the boxes 56 with either the same, if the participants believe both wines have the same amount of that particular characteristic or much more or more, depending on the degree of difference they perceive from the two samples. For example, a participant who determined that the wine in the glass 4 bearing stem tag 2b had the same "sweet/almond" aroma as the wine in the glass 4 bearing stem tag 2c would mark the box 57 designated as "the same." Similarly, if the same participant were to determine that the wine in the glass 4 bearing stem tag 2c had a moderate amount of "sweet/almond" characteristic more than the wine in the glass 4 bearing stem tag 2b, he or she would mark the box 57 toward the right side designated as "more." The scoring in the variants for the comparative evaluations is done in the same manner as for the independent evaluations, i.e., the differences between the participants' ratings and the correct answers are summed to arrive at a total score for the second phase.

The examples described above could also be applied to other parameters that describe the characteristics of wines. Such parameters include acid, tannin, terroir, and age. It should be noted that with respect to the parameters of acid, tannin, and age, the wines are preferably made from the same vintage, varietal, vineyard, and block. The same holds true for terroir and yield, except that the blocks will necessarily have to be different. Similarly, the invention can be adapted to other consumables such as beverages and foods. Examples include a kit comprising beer brewed using the same processes and ingredients except for the variety of hops or a kit comprising two chocolate bars made from cocoa beans from Guatemala and Ghana.

As would be apparent to a person skilled in the art, a number of variations and modifications can be made to the invention described above without departing from its spirit and scope.

The invention claimed is:

1. A method for evaluating sensory characteristics of consumables comprising:
   a step of selecting a first and second consumable, in which each consumable has sensory characteristics that are common to both, wherein the first consumable and the second consumable vary in degree for at least one sensory characteristic;
   a step of placing samples of the first consumable into a first sample container and a second sample container;
   a step of placing samples of the second consumable into a third sample container and a fourth sample container;
   whereas the first consumable and the second consumable vary in at least one characteristic detectable by smell or taste;
   a step of arranging the first, second, third, and fourth sample containers such that a participant is unaware of which of the two consumables is in the four sample containers; a plurality of determination steps in which each of the determination steps comprises selecting three of the sample containers according to a predetermined pattern, and having a participant make a determination of which sample container contains the consumable that is different from the consumable in the other two containers, and making a record of the determination, in which each of the determination steps entails forming a set of three sampling containers that is different from the sets formed in the other determination steps; and
a step of assigning a score to the participant based on a total number of correct determinations made by the participant.

2. The method of claim 1 in which the first consumable has been manufactured in accordance with a first recipe and the second consumable has been manufactured in accordance with a second recipe, said second recipe differing from said first recipe with respect to a single processing parameter or ingredient.

3. The method of claim 1 in which the first, second, third, and fourth sample containers are coded to distinguish them from each other.

4. The method of claim 1 in which the step of placing samples of a first consumable into a first sample container and a second sample container and the step of placing samples of a second consumable into a third sample container and a fourth sample container are performed in accordance with an instruction selected from a plurality of predetermined instructions.

5. The method of claim 1 in which the first, second, third, and fourth sample containers are coded with different letters to distinguish them from each other, and in which the predetermined pattern comprises letters such that words may be formed from a combination of letters on the three selected sample containers.

6. The method of claim 5 in which the step of assigning a score to the participant incorporates an answer key comprising words in which the letters on the sample container that contains the consumable that is different from the consumable in the other two sample containers is typographically distinguishable from the other letters in the words.

7. A method for evaluating sensory characteristics of consumables comprising:
   a step of selecting a first and second consumable, in which each consumable has sensory characteristics that are common to both;
   a step of selecting a set of sensory characteristics that are common to the first and second consumable;
   a step of creating assigned values for each sensory characteristic in the set that reflect a degree of presence of each sensory characteristic in the first consumable;
   a step of creating assigned values for each sensory characteristic in the set that reflect a degree of presence of each sensory characteristic in the second consumable;
   a step of placing a sample of the first consumable into a first sample container;
   a step of placing a sample of the second consumable into a second sample container;
   a step of a participant making an evaluation of each of the sensory characteristics of the consumables in the first and second sample containers and recording the participant's determination of a value that best reflects the participant's opinion of a degree of presence of each of the sensory characteristics; and
   a step of calculating a total score that reflects a proximity of the participant's determination of the value to the assigned value of each of the sensory characteristics in each of the samples of the first and second consumables present in the first and second containers.

8. The method of claim 7 in which the step of a participant making an evaluation of each of the sensory characteristics of the consumables in the first and second sample containers and recording the participant's determination of a value that best reflects the participant's opinion of a degree of presence of each of the sensory characteristics encompasses substeps of:
   a substep of the participant making an evaluation of each of the sensory characteristics of the consumable in the first sample container and recording the participant's determination of a value that best reflects the participant's opinion of a degree of presence of each of the sensory characteristics;
   a substep of the participant making an evaluation of each of the sensory characteristics of the consumable in the second sample container and recording the participant's determination of a value that best reflects the participant's opinion of a degree of presence of each of the sensory characteristics;

and further in which the step of calculating a score that reflects the proximity of the participant's determination of the value to the assigned value of each of the sensory characteristics comprises the following substeps:

a substep of calculating a first subscore for the consumable in the first sample container that reflects the proximity of the participant's determination of the value to the assigned value of each of the sensory characteristics;

a substep of calculating a second subscore for the consumable in the second sample container that reflects the proximity of the participant's determination of the value to the assigned value of each of the sensory characteristics; and a substep of combining the subscores for the consumables in the first and second sample containers to determine the total score.

9. The method of claim 7 in which the sensory characteristics are quantified via a chemical analysis and the assigned values are based on results of the chemical analysis.

10. The method of claim 7 in which the first consumable has been manufactured in accordance with a first recipe and the second consumable has been manufactured in accordance with a second recipe, said second recipe differing from said first recipe with respect to a single processing parameter or ingredient.

11. The method of claim 7 in which the first and second sample containers are arranged such that the participant is unaware of which of the two consumables is in the first and second containers and having a final step of asking the participant to identify the first and second consumables.

12. A method for evaluating sensory characteristics of consumables comprising:

a step of selecting a first and second consumable, in which each consumable has sensory characteristics that are common to both, wherein the first consumable and the second consumable vary in degree for at least one sensory characteristic;

a step of creating assigned values for each sensory characteristic in a first set that reflects a degree of presence of each sensory characteristic in the first consumable;

a step of creating assigned values for each sensory characteristic in a second set that reflects a degree of presence of each sensory characteristic in the second consumable;

a step of placing samples of the first consumable into a first sample container and a second sample container;

a step of placing samples of the second consumable into a third sample container and a fourth sample container;

a step of arranging the first, second, third and fourth sample containers such that a participant is unaware of which of the two consumables is in the four sample containers;

a plurality of decision steps in which each of the decision steps comprises selecting three of the sample containers according to a predetermined pattern, and having a participant decide which sample container contains the consumable that is different from the consumable in the other two containers, and making a record of the decision, in which each of the decision steps entails forming a set of three sampling containers that is different from the sets formed in the other decision steps;

a step of assigning a first score to the participant based on a total number of correct decisions made by the participant;

a step of arranging the second and third sampling containers such that a participant is unaware of which of the two consumables is in the second and third sample containers;

a plurality of determination steps in which each of the determination steps comprises the participant making an evaluation of one of the sensory characteristics of the consumable in the second and third sample containers and recording the participant's determination of a value that best reflects the participant's opinion of a degree of presence of each of the sensory characteristics;

a step of calculating a second score for the consumables in the second and third sample containers that reflects a proximity of the participant's determination of the value to the assigned value of each of the sensory characteristics in each of the samples of the first and second consumables present in the second and third containers; and a step of combining the first and second scores to determine a total score.

13. The method of claim 12 in which the first consumable has been manufactured in accordance with a first recipe and the second consumable has been manufactured in accordance with a second recipe, said second recipe differing from said first recipe with respect to a single processing parameter or ingredient.

14. The method of claim 12 in which the first, second, third, and fourth sample containers are coded to distinguish them from each other.

15. The method of claim 12 in which the step of placing samples of a first consumable into a first sample container and a second sample container and the step of placing samples of a second consumable into a third sample container and a fourth sample container are performed in accordance with an instruction selected from a plurality of predetermined instructions.

16. The method of claim 12 in which the first, second, third, and fourth sample containers are coded with different letters to distinguish them from each other, and in which the predetermined pattern comprises letters such that words may be formed from a combination of letters on the three selected sample containers.

17. The method of claim 16 in which the step of assigning the first score to the participant incorporates an answer key comprising the words formed by the combination of letters on the three selected sample containers corresponding to different predetermined patterns, wherein a single letter in each word of the answer key is typographically distinguishable from the other letters in each word, and the letter which is typographically distinguishable from the other letters corresponds to the sample container that contains the consumable that is different from the consumable in the other two sample containers.

18. The method of claim 12 in which the sensory characteristics are quantified via a chemical analysis and the assigned values based on results of the chemical analysis.

19. The method of claim 12 in which the plurality of determination steps in which each of the determination steps comprises the participant making an evaluation of one of the sensory characteristics of the consumable in the second and third sample containers and recording the participant's determination of a value that best reflects the participant's opinion of a degree of presence of each of the sensory characteristics further comprise the substeps of:

the participant making an evaluation of each of the sensory characteristics of the consumable in the second sample container and recording the participant's determination of a value that best reflects the participant's opinion of a degree of presence of each of the sensory characteristics, in which each of the determination steps entails an evaluation of a sensory characteristic that is different from the sensory characteristics evaluated in the other determination steps; and     the participant making an evaluation of each of the sensory characteristics of the consumable in the third sample container and recording the participant's determination of a value that best reflects the participant's opinion of a degree of presence of each of the sensory characteristics, in which each of the determination steps entails an evaluation of a sensory characteristic that is different from the sensory characteristics evaluated in the other determination steps;

and further in which the step of calculating a second score for the consumables in the second and third sample containers that reflects a proximity of the participant's determination of the value to the assigned value of each of the sensory characteristics comprises the substeps of     calculating a first subscore for the consumable in the second sample container that reflects a proximity of the participant's determination of the value to the assigned value of each of the sensory characteristics; and     calculating a second subscore for the consumable in the third sample container that reflects a proximity of the participant's determination of the value to the assigned value of each of the sensory characteristics; and     combining the first and second subscores to determine the second score.

\* \* \* \* \*